United States Patent [19]

Redikultsev et al.

[11] Patent Number: 4,689,306
[45] Date of Patent: Aug. 25, 1987

[54] DEVICE FOR STERILE SAMPLING FROM A FERMENTER

[75] Inventors: Jury V. Redikultsev, Moskovskoi; Jury G. Zanin, Moscow; Alexandr N. Shkidchenko, Moskovskoi; Oleg P. Gorbunov, Moskovskoi; Mikhail G. Maximov, Moskovskaya; Taisia S. Chermenskaya, Moskovskoi, all of U.S.S.R.

[73] Assignee: Institut Biokhimii I Fiziologii Mikroorganizmov Akademii Nauk SSSR, Moscow, U.S.S.R.

[21] Appl. No.: 551,981
[22] PCT Filed: Mar. 19, 1982
[86] PCT No.: PCT/SU82/00012
 § 371 Date: Oct. 31, 1983
 § 102(e) Date: Oct. 31, 1983
[87] PCT Pub. No.: WO83/03302
 PCT Pub. Date: Sep. 29, 1983
[51] Int. Cl.$^4$ .................. C12M 1/26; C12M 1/28; C12M 1/12; C12Q 1/24
[52] U.S. Cl. .................... 435/292; 435/30; 435/294; 435/311; 422/101; 422/103; 73/863.23
[58] Field of Search ............... 435/287, 292, 293, 294, 435/296, 311, 30; 422/101, 102, 103, 119; 73/863.86, 864.52, 864.63, 863.23; 141/349

[56] References Cited

U.S. PATENT DOCUMENTS

| | | | |
|---|---|---|---|
| 1,948,271 | 2/1934 | Loughlin | 435/292 |
| 2,989,091 | 6/1961 | Lowenthal | 141/349 X |
| 3,013,950 | 12/1961 | Gavin | 435/316 X |
| 3,035,617 | 5/1962 | Breitenstein | 141/349 |
| 3,115,907 | 12/1963 | Labat | 141/349 X |
| 3,181,737 | 5/1965 | Chaucer | 141/349 X |
| 3,198,016 | 8/1965 | Poorman | 73/863.86 |
| 3,682,596 | 8/1972 | Stone | 422/101 |
| 4,021,120 | 5/1977 | Muller et al. | 435/808 X |

FOREIGN PATENT DOCUMENTS

| | | | |
|---|---|---|---|
| 2016079 | 10/1971 | Fed. Rep. of Germany | 73/863.86 |
| 2723240 | 11/1978 | Fed. Rep. of Germany | 435/294 |
| 1201524 | 12/1959 | France | 141/349 |
| 597938 | 2/1978 | U.S.S.R. | |

OTHER PUBLICATIONS

P. I. Voskresenskii, "Tekhnica Laboratornikh Rabot", 1966 Khimia, Moscow, p. 83—plus English translation.
The Bench Top Chemostat, Model C30, 1971 New Brunswick Scientific Co., Inc.
New Brunswick Scientific Co., Inc., Catalog 377, pp. C-43 and C-44.

Primary Examiner—Robert J. Warden
Assistant Examiner—Randall E. Deck
Attorney, Agent, or Firm—McAulay, Fields, Fisher, Goldstein & Nissen

[57] ABSTRACT

A device of the present invention for sterile sampling of culture liquor from a fermenter comprises a sampler (1) positioned on the fermenter (3) in the zone of stirring the culture liquor and a sterile sample collector (11). The sampler (1) is fashioned as a normally closed valve whose body (4) has a circular projection (8) on the side of contact with the sample collector (11). The sample collector (11) is made evacuated and has a normally closed valve (12) mounted on its neck, the body (13) of which on the side of contact with the sampler (1) is provided a circular groove (17) conjugated with the circular projection (8) of the sampler (1). Upon superposition and interaction of the latter is formed a sealed conduit (19) for the passage of culture liquor from the fermenter (3) to the sample collector (11).

6 Claims, 2 Drawing Figures

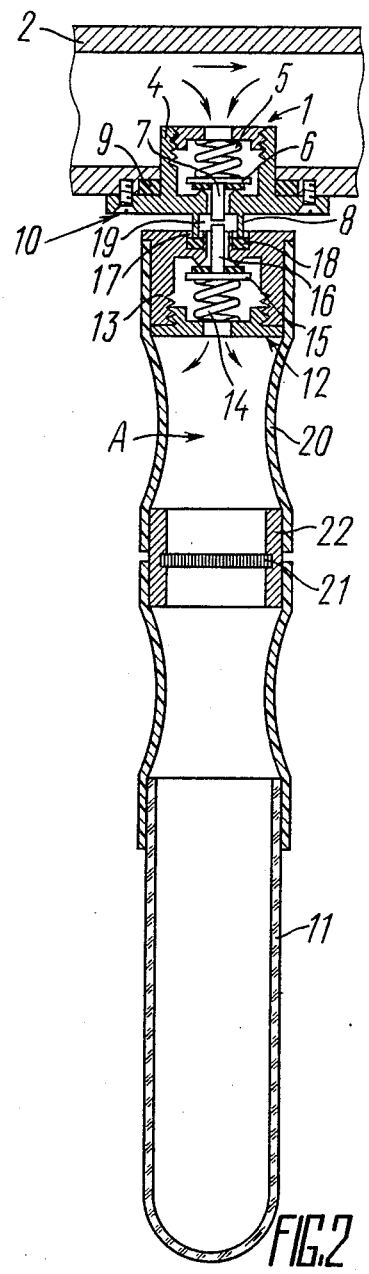

DEVICE FOR STERILE SAMPLING FROM A FERMENTER

TECHNICAL FIELD

The present invention relates to apparatus for microbiological studies and, more particularly, it relates to a device for sterile sampling from a fermenter.

BACKGROUND OF THE INVENTION

The sterile sampling of culture liquor from a fermenter is essential for effecting control over the state of the object under study and determining the conditions of its active life environment. All of the laboratory-type and commercial fermenters are provided with devices for sterile sampling of culture liquor. In spite of a great diversity of fermenter designs, there is little structural difference between the various devices for sterile sampling of culture liquor. The sampling of culture liquor from a fermenter is done manually and involves certain operations that are to be performed simultaneously with each other. The sampling is usually done by two researchers, to which end a plug is removed from a sterile sampler in the flame of an alcohol burner and a clamp is released on the culture liquor drain pipe, or valves are operated. The duration of sampling does not enable one to analyze the status of transient processes of microorganism development, which is of special research importance. This latter consideration gave a start to the search for novel structural solutions of devices for sterile sampling of culture liquor from a fermenter.

There is known in the art a device for sterile sampling from a fermenter (cf., data sheet by New Brunswick Scientific Co., Inc., on Model FM 250), comprising a drain pipe with a valve, positioned on the fermenter and having an outlet connection communicating with a steam delivery pipeline. For sampling culture liquor from the fermenter, one should first sterilize a sample collector plugged with a cotton-wool or some other readily removable stopper. Then, the sample collector is connected with the outlet connection and sterilized with steam, and the sampling valve is opened.

When using the afore-described device, part of the culture liquor from the pipeline is to be drained off, this resulting in undesirable losses of culture liquor, especially when carrying out periodic processes of microorganism growing. In addition, the use of this prior art device requires that the culture liquor in the fermenter should always be under excess pressure which is not always convenient and possible in the course of growing microorganisms, or that a transfer pump be used in the drain line. Steam is discharged via outlet connection to the working premises, which aggravates the working conditions of the personnel.

Well known in the art is a device for sterile sampling from a fermenter using antiseptics such as chloramine, comprising a pipeline with a valve for the passage of culture liquor from the fermenter and a pipeline with a valve for the passage of the antiseptic. After the valves, the pipelines are combined in a single line provided with an outlet connection. Cotton wool-plugged test tubes are used as sterilized sample collectors. For sampling, the culture liquor drain valve is opened and, following partial drain of said liquor, the sample collector plug is removed and the sample collector is placed under the stream of liquor. After the requisite amount of culture liquor has been collected, the sample collector is plugged and the drain valve closed. After that, the valve on the antiseptic pipeline is opened and the antiseptic is partly drained; in so doing, the antiseptic should stay in the outlet connection until the next sampling.

This latter prior art device provides for additional drain from the zone of culture liquor stagnation, which leads eventually to losses of said liquor. Also, upon preliminary partial drain of the culture liquor some antiseptic stays on the walls of the outlet connection, which results in the presence of antiseptic in the sample collector and, consequently, in distortion of the analysis results, especially in the case of enzymes.

There is also known a device for sterile sampling from a fermenter, comprising a sampler positioned on the fermenter in the zone of stirring of culture liquor, and a sterile sample collector (cf., data sheet by New Brunswick Scientific Co., Inc., on BIOFLO Model C 30).

This latter device also comprises a drain pipe with a screw clamp, on which pipe there is secured a chamber with a rubber spray bulb or injector, and a joining unit. The sterilized sample collector is set up and joined to the joining unit under the flame of a burner. Sampling is effected in the following manner. Pressure is applied to the rubber bulb while the screw clamp is released, the air being forced from the sample collector to the fermenter. A release of the rubber bulb results in the restoration of its shape and, simultaneously, in the inflow of culture liquor from the fermenter to the sample collector. After that, the screw clamp is closed and the sample collector with sample is replaced with a sterilized empty sample collector under the flame of a burner.

The use of the last-described prior art device requires that a researcher should perform in the course of sampling a whole series of successive operations, which results in considerable time consumption. As a result, one cannot take a substantial number of samples per unit time, as required for the purposes of studying the dynamics of microorganism growth. The use of open flame in the course of connection and removal of the sample collector prohibits the utilization of the device for operation with explosive gases which provide the environment for the growth of some microorganisms. It is not always desirable to return the air to the fermenter upon pressing the rubber bulb, while in the case of microorganisms growing under conditions of a strict ratio of the supplied gases, such as hydrogen-oxidizable bacteria, it is simply inadmissible. Moreover, said prior art device also suffers from the loss of culture liquor which should always be drained from the stagnation zone of the drain pipe prior to sampling.

OBJECTS AND SUMMARY OF THE INVENTION

The main object of the present invention is to provide a device for sterile sampling of culture liquor from a fermenter with a sampler and its connection with a collector which would help considerably reduce the sampling time, to maintain the sample sterility, to preclude the loss of culture liquor upon sampling, to prepare a filter liquor upon sampling directly from the fermenter and to provide for the visualization of the sample collector sterility.

In the accomplishment of the object of the present invention, in a device for sterile sampling of culture liquor from a fermenter, comprising a sampler positioned on the fermenter in the zone of stirring the culture liquor and a sterile probe collector, according to the invention, the sample collector upon sampling is placed on the sampler and communicates therewith, the sampler being a normally closed valve whose body has a circular projection on the side of contact with the sample collector which is made evacuated and has a normally closed valve mounted on its neck, the body of said latter valve being provided, on the side of contact with the sampler, with a circular groove having a seal and conjugated with the circular projection of the sampler such that said groove and said projection form, upon superposition and interaction, a sealed conduit for the passage of culture liquor from the fermenter to the sample collector.

It is expedient that the normally closed valve be mounted on the neck of the sample collector with the aid of an elastic collar.

Preferably, a bacteriological filter is provided in the elastic collar between the normally closed valve and the neck of the sample collector.

The herein disclosed device for sterile sampling from a fermenter enables a single researcher to do the sampling and, at the same time, reduce considerably the time required for a single sampling. The evacuated sample collector helps maintain the sample sterility and ensure a prolonged storage of the sterile sample. The absence of any stagnation zones helps fully preclude the loss of culture liquor upon sampling. The elastic collar placed on the neck of the sample collector helps ensure the visualization of the pressure-tightness or the sterility of the latter while ruling out the possibility of sampling into a non-sterile sample collector.

BRIEF DESCRIPTION OF THE DRAWINGS

The present invention is further exemplified by the description of specific embodiments thereof, with due references to the accompanyings, in which:

FIG. 2 is the device shown in FIG. 1 provided with an elastic collar in which is mounted a bacteriological filter, according to the present invention.

BEST MODE FOR CARRYING OUT THE INVENTION

Figure 1:
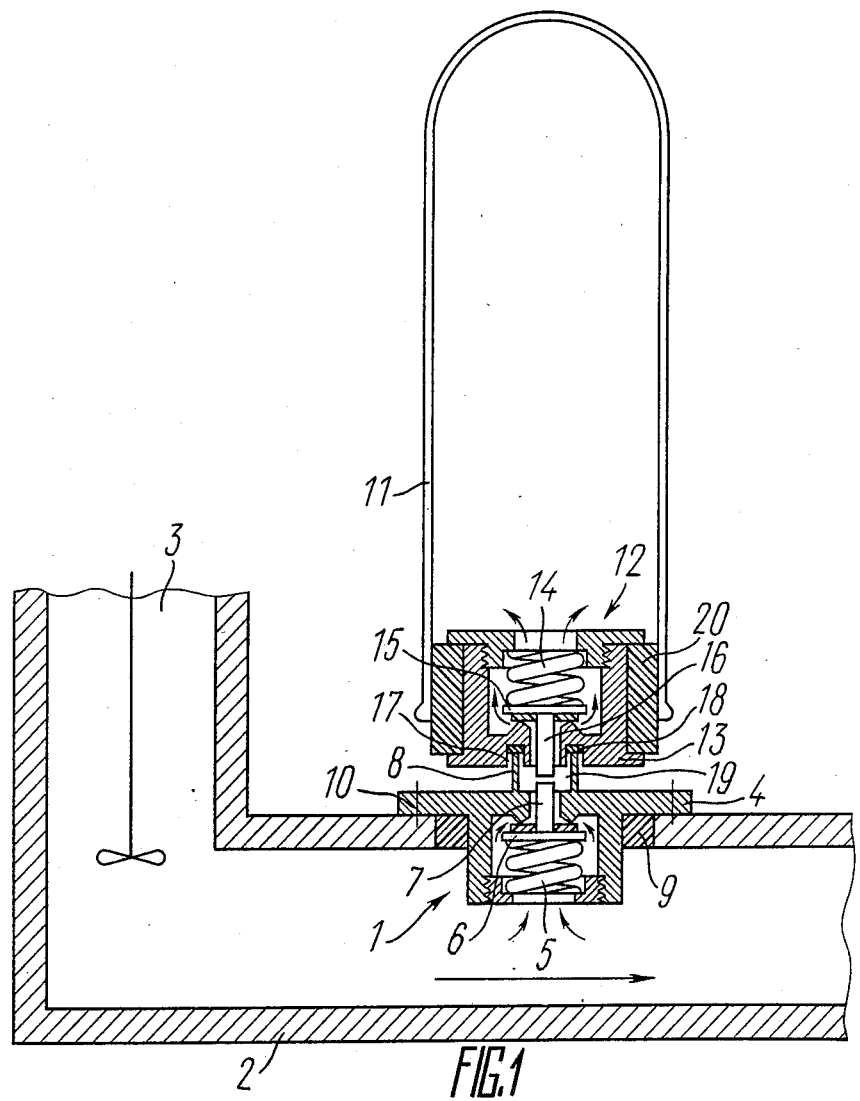
FIG. 1 illustrates the device for sterile sampling from a fermenter (longitudinal section) according to the present invention.

The herein disclosed device for sterile sampling from a fermenter comprises a sampler 1 (FIG. 1) positioned on a pipeline 2 serving for the recirculation of culture liquor from a fermenter 3. The sampling of the culture liquor is done from a zone of vigorous stirring thereof.

The sampler 1 is fashioned as a normally closed valve including a body 4, a spring 5 and a cut-off member 6 located on a rod 7. The body 4 has a circular projection 8. The body 4 of the normally closed valve is mounted in the pipeline 2 with the aid of a spacer 9 and a screw joint 10 (conventionally shown).

The device of the invention further comprises a sterile sample collector 11 such as the evacuated test tube used in the embodiment described herein. Mounted on the neck of the sample collector 11 is a normally closed valve 12 analogous with that described above and including a body 13, a spring 14 and a cut-off member 15 located on a movable rod 16. The body 13 has a circular groove 17 with a seal 18, conjugated with the circular projection 8 of the sampler 1. The projection 8 and groove 17 form, upon superposition and interaction, a sealed conduit 19 for the passage of culture liquor from the fermenter 3 to the sample collector 11.

The normally closed valve 12 is mounted on the neck of the sample collector 11 by means of an elastic collar 20 which, in the herein described embodiment, is located inside the sample collector 11 together with the valve 12.

One of the embodiments of the present invention is when the elastic collar 20 (FIG. 2) is elongated and embraces by one of its sides the neck of the sample collector 11, and by its other side the body 13 of the normally closed valve 12. It is convenient that, firstly, to indicate vacuum in the sample collector 11 as in this case the elastic collar 20 is compressed or depressed, and secondly, it makes it possible to use as the sample collectors 11 capacities of various volumes depending on the required volume of a sample.

To adsorb microorganims and obtain a filtrate for a culture liquor without centrifuging in the elastic collar 20 between the normally closed valve 12 and the neck of the sample collector 11 is mounted a bacteriological filter 21 in the casing 22.

The device of the present invention for sterile sampling from a fermenter operates as follows.

A researcher positions the sterile evacuated sample collector 11 (FIG. 1) on the sampler 1 such that the circular projection of the sampler 1 enter the circular groove 17 of the sample collector 11. This results in the formation of the conduit 19 sealed by means of an elastic ring 18. A subsequent pressure against the sample collector such that the direction of the pressing force coincide with the longitudinal axis of the valve 12 causes the rods 7 and 16 to interact. As a result, the springs 5 and 14 compress to open the cut-off members 6 and 15 and release the conduit 19 through which the culture liquor flows over from the fermenter 3 to the sample collector 11. After sampling the required amount of culture liquor, the researcher relieves the pressure, the springs 5 and 14 restoring the initial normally closed position of the cut-off members 6 and 15.

The sterile sampling from the fermenter 3 is done as follows.

From a set of sterilized and evacuated sample collectors 11, the researcher selects those with flattened elastic collars 20 indicative of the vacuum maintained in the sample collector. Further, the researcher performs sampling steps similar to those described above. The culture liquor flows via the sealed conduit 19 over to zone A of the elastic collar 20. After sampling, the researcher relieves the pressing force and the cut-off members 6 and 15 return to the normally closed position, the elastic collar 20 expanding. Then, the sample collector 11 is placed vertically in a rack, with the valve 12 upwards. In the sample collector 11 and zone A of the elastic collar 20 there takes place an equalization of pressure owing to the passage of culture liquor from the zone A via bacteriological filter 21 to the sample collector 11. In so doing, the elastic collar 20 gets flattened once again.

INDUSTRIAL APPLICABILITY

The herein disclosed device can be used in microbiological, medical, chemical and food industries, as well as in everyday scientific studies for the sterile sampling of a culture liquor.

What is claimed is:

1. A device for the sterile sampling from a fermenter having a wall and a pipeline for recirculating culture liquor comprising:
   a sampler positioned on the pipeline;
   said sampler comprising a first valve extending outside beyond said pipeline;
   said first valve having a rod, a cut-off member coupled with said rod, and a spring coupled with said cut-off member to maintain said first valve in a closed position when no force is applied to said rod;
   an external circular projection on said valve concentric with said rod;
   a sterile sample collector comprising an evacuated container having an inlet;
   a second valve mounted on said inlet of said container;
   an elastic collar placed between said second vlave and said inlet of said container;
   said second valve having a rod extending outside beyond said container;
   a cut-off member on said second valve coupled with said rod of said second valve;
   a spring on the second valve coupled with said cut-off member of the second valve for maintaining said second valve in the closed position when no force is applied to said rod;
   an external circular groove provided in said second valve concentrically with said rod thereof; and
   a seal placed in said circular groove;
   said circular projection and said circular groove with said seal forming together a sealed conduit between said valves,
   said rod of said first valve and said rod of said second valve being disposed one opposite to the other in said sealed conduit;
   said elastic collar defining an additional space between said second valve and said container, said collar insuring the visualization of the vacuum or the sterility of the container while eliminating the possiblity of sampling into a non-sterile collector.

2. A device as claimed in claim 1, comprising a bacterial filter arranged in said additional space.

3. The device of claim 1, wherein said sample collector has a neck portion and said second valve is mounted on said neck portion by means of said elastic collar, said second valve being located in said elastic collar.

4. The device of claim 2 wherein said sample collector has a neck portion and said second valve is mounted on said neck portion by means of said elastic collar, said second valve being located in said elastic collar.

5. In a device for the sterile sampling from a fermenter, said fermenter having a wall, and a stirring zone for culture liquor and comprising:
   a sampler positioned in said stirring zone and comprising a first valve;
   said first valve extending outside beyond said wall;
   said first valve including a rod, a cut-off member coupled with said rod and a first spring coupled with said cut-off member to maintain said valve in a closed position when no force is applied to said rod;
   an external circular projection on said first valve concentric with said rod;
   a sterile sample collector comprising an evacuated container having a neck and an inlet;
   a second valve mounted on the inlet of said container;
   an elastic collar placed between said second valve and said inlet of said container;
   said second valve including a second rod extending outside beyond said container;
   a cut-off member on said second valve coupled with said rod of said second valve;
   a second spring, said second spring being on said second valve coupled with said cut-off member of said second valve for maintaining said second valve in the closed position when no force is applied to said rod of said second valve;
   an external circular groove provided in said second valve concentrically with said rod thereof;
   a seal placed in said circular groove;
   said circular projection and said circular groove with said seal forming together a sealed conduit between said valves; and
   said rod of said first valve and said rod of said second valve being disposed one opposite to the other in said sealed conduit; and
   the improvement comprising:
      said elastic collar defining an additional space between said second valve and said container, said collar insuring the visualization of the vacuum or the sterility of the container while eliminating the possiblity of.sampling into a non-sterile collector; and
      a bacterial filter positioned in said additional space.

6. The device of claim 5, wherein said second valve is mounted on said inlet portion by means of said elastic collar, said second valve being located in said elastic collar.

* * * * *